United States Patent
Boffelli et al.

(10) Patent No.: US 8,071,788 B2
(45) Date of Patent: Dec. 6, 2011

(54) METHOD AND INTERMEDIATES FOR THE PREPARATION OF DERIVATIVES OF N-(1-BENZHYDRYLAZETIDIN-3-YL)-N-PHENYLMETHYLSULFONAMIDE

(75) Inventors: Philippe Boffelli, Rosny Sous Bois (FR); Michel Delthil, Noisy le Sec (FR); Luc Grondard, Courcouronnes (FR); Maxime Lampilas, Romainville (FR); Joel Malpart, Olivet (FR); Stephane Mutti, Perreux sur Marne (FR); Lahlou Nait-Bouda, Thiais (FR); Joerg Reike-Zapp, Frankfurt (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/635,965

(22) Filed: Dec. 11, 2009

(65) Prior Publication Data

US 2010/0087414 A1 Apr. 8, 2010

Related U.S. Application Data

(60) Division of application No. 12/194,644, filed on Aug. 20, 2008, now Pat. No. 7,652,154, which is a division of application No. 11/692,462, filed on Mar. 28, 2007, now Pat. No. 7,429,668, which is a continuation of application No. PCT/FR2005/002489, filed on Oct. 10, 2005.

(30) Foreign Application Priority Data

Oct. 14, 2004 (FR) .................................... 04 10845

(51) Int. Cl.
*C07D 205/04* (2006.01)
*C07C 211/01* (2006.01)

(52) U.S. Cl. ........................................ 548/952; 564/321

(58) Field of Classification Search ............. 514/210.01; 564/321, 124, 130; 548/952
See application file for complete search history.

(56) References Cited

U.S. PATENT DOCUMENTS 6,566,356 B2 * 5/2003 Achard et al.

FOREIGN PATENT DOCUMENTS

WO WO 01/64634 * 9/2001
WO WO 02/28346 * 4/2002

OTHER PUBLICATIONS

Gullickson et al., Synthesis of N-Benzhydrylamides from Nitriles by Ritter Reactions in Formic Acid, 2003, Synthesis, No. 5, 681-684.*
Salehi et al., Facile Conversion of Alcohols into N-Substituted Amides by Magnesium Hydrogensulfate Under Heterogeneous Conditions, 2001, Synthetic Communications, 31(13), 1947-1951.*
Formic acid [online], [retrieved on Mar. 17, 2011]. Retrieved from the Internet, URL:http://en.wikipedia.org/wiki/Formic_acid.*
Gakhar, H.K., et al., A New Method of Preparation of 1,3-dioxolo[4,5-h] [1,4]Benzodiazepin-9-ones, Indian Journal of Chemistry vol. 34B, (1995) pp. 48-50.
Zubovics, Z., et. al.,, Synthesis and Antiarrhythmic Activity of N-aryl Alkylenediamines, Eur. J. Med. Chem. Ther. (1986) vol. 21, No. 5, pp. 370-378.
The Metabolic Syndrome, http://www.diabetes.org/weightloss-and-exercise/weightloss/metabollicsyndrome.jsp (2005).
Annual Update 2003/2004—Treatment of Neurological Disorders, Drugs of the Future (2004), vol. 29, No. 3, pp. 253-317.

* cited by examiner

*Primary Examiner* — Kamal Saeed
*Assistant Examiner* — Kristin Bianchi
(74) *Attorney, Agent, or Firm* — Scully, Scott, Murphy & Presser, P.C.

(57) ABSTRACT

The invention relates to a novel method for the synthesis of N-{1-[bis(4-chlorophenyl)methyl]azetidin-3-yl}-N-(3,5-difluorophenyl)methylsulfonamide.

2 Claims, No Drawings

METHOD AND INTERMEDIATES FOR THE PREPARATION OF DERIVATIVES OF N-(1-BENZHYDRYLAZETIDIN-3-YL)-N-PHENYLMETHYLSULFONAMIDE

CROSS REFERENCE TO RELATED APPLICATIONS

This application is a divisional of U.S. application Ser. No. 12/194,644, filed Aug. 20, 2008, now allowed, which is a divisional of U.S. application Ser. No. 11/692,462, filed Mar. 28, 2007, now U.S. Pat. No. 7,429,668 B2, issued, Sep. 30, 2008, which is a continuation of International application No. PCT/FR2005/002,489, filed Oct. 10, 2005, all of which are incorporated herein by reference in their entirety; which claims the benefit of priority of French Patent Application No. 04/10,845, filed Oct. 14, 2004.

BACKGROUND OF THE INVENTION

1. Field of the Invention

The present invention relates to processes for preparing azetidine derivatives of N-(1-benzhydrylazetidin-3-yl)-N-phenylmethylsulfonamide (I) and in particular N-{1-[bis(4-chlorophenyl)methyl]azetidin-3-yl}-N-(3,5-difluorophenyl)methylsulfonamide.

2. Description of the Art

These products are described in patent application WO 01/64634, which is incorporated herein by reference in its entirety. These products are known as having high affinity for cannabinoid receptors and particularly those of CB1 type and are thus useful in the treatment and prevention of disorders affecting the central nervous system, the immune system, the cardiovascular or endocrine system or the respiratory system, and reproductive disorders. Thus, these compounds may be used for treating or preventing psychoses, including schizophrenia, anxiety disorders, depression, epilepsy, neurodegeneration, cerebellar and spinocerebellar disorders, cognitive disorders, head injuries, panic attacks, peripheral neuropathy, glaucoma, migraine, Parkinson's disease, Alzheimer's disease, Huntington's chorea, Reynaud's disease, tremor, obsessive compulsive disorder, senile dementia, thymus disorders, Tourette's syndrome, tardive dyskinesia, bipolar disorders, cancers, drug-induced locomotor disorders, dystonia, endotoxaemic shock, hemorrhagic shock, hypotension, insomnia, immunological diseases, multiple sclerosis, vomiting, asthma, eating disorders (bulimia or anorexia), obesity, memory disorders, in weaning from chronic treatments and alcohol or drug (opioids, barbiturates, cannabis, cocaine, amphetamine, phencyclidine, hallucinogen or benzodiazepines, for example) abuse, as analgesics or as potentiators of the analgesic activity of narcotic and non-narcotic drugs.

The present invention also relates to the use of N-{1-[bis(4-chlorophenyl)methyl]azetidin-3-yl}-N-(3,5-difluorophenyl)methylsulfonamide in the treatment of metabolic syndrome and visceral obesity.

SUMMARY OF THE INVENTION

The present invention relates to the preparation of N-(1-benzhydrylazetidin-3-yl)-N-phenylmethylsulfonamide derivatives of general formula (I) in which R, R' and R" represent, independently of each other, one or more hydrogen, halogen (Cl, F, Br or I), cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy radicals and R''' represents a linear or branched alkyl or perfluoroalkyl group of 1 to 6 carbon atoms or an aryl group optionally substituted with one or more radicals R".

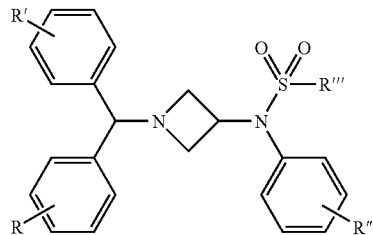

DETAILED DESCRIPTION OF THE INVENTION

Patent application WO 01/64634 describes general routes of access for obtaining such products and in particular a synthesis via condensation of a sulfonate and a sulfonamide in an inert solvent such as dioxane, in the presence of $Cs_2CO_3$ at the reflux temperature of the reaction mixture.

The compound of formula (I) is obtained by condensing a sulfonate of general formula (II) and a sulfonamide of general formula (III) in which R, R' and R" represent, independently of each other, one or more hydrogen, halogen (Cl, F, Br or I), cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy radicals and R''' represents a linear or branched alkyl or perfluoroalkyl group of 1 to 6 carbon atoms or an aryl group optionally substituted with one or more radicals R" and R1 represents a methyl, trifluoromethyl, $C_4F_9$, $C_8F_{17}$ or phenyl radical optionally substituted with a methyl, bromo or nitro residue.

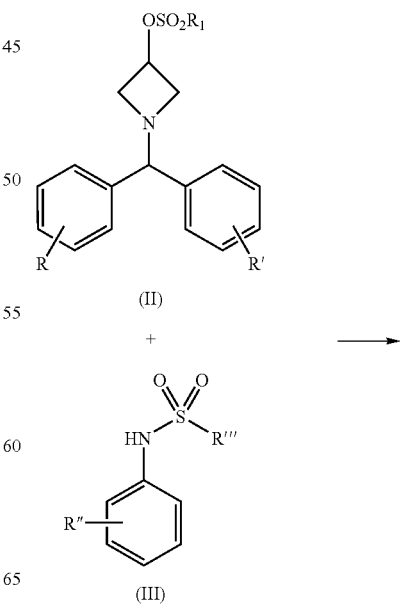

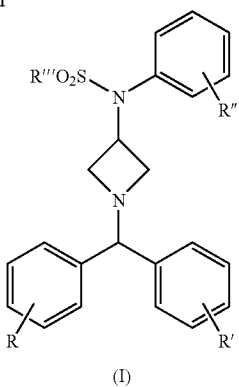

(I)

The condensation is performed in an organic solvent optionally in the presence of water, at a temperature of between 20° C. and 150° C. in the presence of mineral or organic base and of a phase-transfer agent.

The process is preferably performed in a solvent such as toluene or xylene. Other solvents may be used, such as heptane, hexane, an ether solvent such as tetrahydrofuran or dimethoxyethane, or alternatively a chlorinated solvent such as monochlorobenzene, dichlorobenzene, chlorobutane or methylene chloride, alcohols such as methanol, ethanol, isopropanol or butanol, acetonitrile, pyridine, dipolar aprotic solvents such as DMF, dimethylacetamide or N-methylpyrrolidone, and ketones such as acetone, methyl ethyl ketone or methyl isobutyl ketone. A mineral or organic base such as the hydrogen carbonate, carbonate, phosphate or hydroxide of an alkali metal such as lithium, sodium, potassium or cesium, and more particularly anhydrous tripotassium phosphate, is also used. Alkali metal alkoxides such as sodium or potassium methoxide, ethoxide, t-amyloxide or t-butoxide may also be used. Finally, amine bases such as 1,8-diazabicyclo[5.4.0]undec-7-ene (DBU), 1,5-diazabicyclo[4.3.0]non-5-ene (DBN) or tetramethylguanidine may be used. The reaction is performed in the presence of a phase-transfer agent such as a quaternary ammonium salt or a complexing agent. The term "quaternary ammonium salt" means a tetraalkylammonium or benzyltrialkylammonium halide, hydroxide, sulfate or hydrogen sulfate. The alkyl groups correspond to those commonly used by a person skilled in the art, such as a linear alkyl group of 1 to 16 carbon atoms. The terms "complexing agent" and "phase-transfer agent" mean crown ethers such as 12-Crown-4 (12-C-4), 15-Crown-5 (15-C-5) or 18-Crown-6 (18-C-6), pentaglyme (Glyme-6) or polyethylene glycol, PEG 400 and, more particularly, tris(dioxa-3,6-heptyl)amine (TDA-1).

A subject of the invention is also a process characterized in that the compound of formula (II) is obtained by treating a compound of general formula (IV) or an acid salt thereof with a sulfonyl chloride or a sulfonic anhydride in the presence of base at a temperature of between −60° C. and 100° C. The expression "sulfonyl chloride or sulfonic anhydride" means methanesulfonyl chloride or methanesulfonic anhydride, perfluoroalkanesulfonic anhydrides of 1 to 9 carbon atoms, and benzenesulfonyl, p-toluenesulfonyl, p-nitrobenzenesulfonyl or p-bromobenzenesulfonyl chloride. The term "acid salt" means a hydrochloride, hydrobromide, sulfate, hydrogen sulfate, sulfonate such as methanesulfonate or p-toluenesulfonate, or a carboxylic acid salt such as an acetate, an oxalate or a fumarate. Preferably, R''' is a methyl.

The process is preferably performed in a solvent such as toluene, xylene, heptane, hexane, an ether solvent such as tetrahydrofuran or dimethoxyethane, or a chlorinated solvent such as monochlorobenzene, dichlorobenzene, chlorobutane or methylene chloride, acetonitrile, or dipolar aprotic solvents such as DMF, dimethylacetamide or N-methylpyrrolidone, and in the presence of a base such as the hydrogen carbonate, carbonate, phosphate or hydroxide of an alkali metal such as lithium, sodium, potassium or cesium. Amine bases such as triethylamine, diisopropylethylamine, N,N-dimethylaniline, N-methylimidazole, pyridine, DBU, DBN or tetramethylguanidine may also be used.

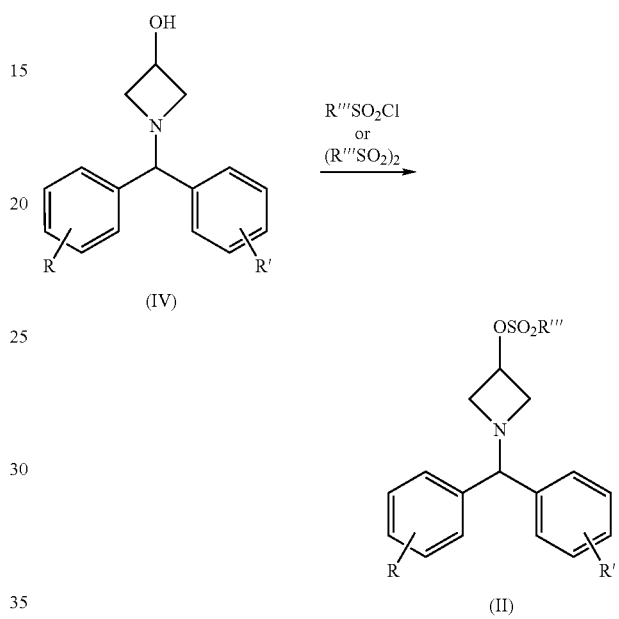

A subject of the invention is also a process characterized in that the compound of formula (IV) is obtained by treating a compound of general formula (V) or an acid salt thereof with epibromohydrin or epichlorohydrin at a temperature of between 20° C. and 150° C.

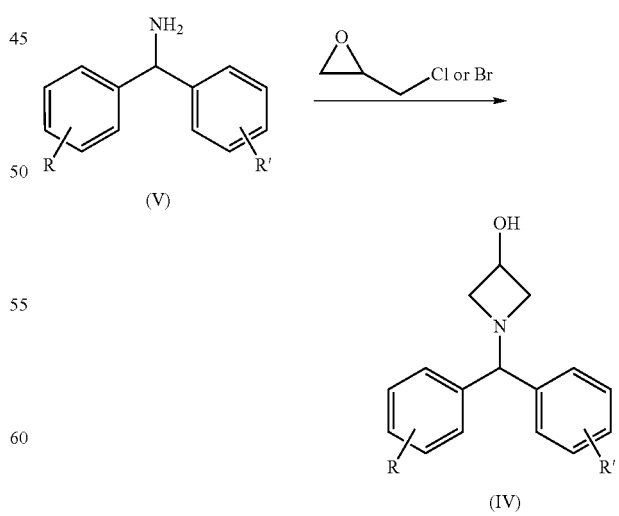

The process is preferably performed in an organic solvent in the presence of base, an additive and, where appropriate, an aqueous phase.

The term "acid salt" means a hydrochloride, hydrobromide, sulfate, hydrogen sulfate, sulfonate such as methanesulfonate or p-toluenesulfonate, or a carboxylic acid salt such as an acetate, an oxalate or a fumarate.

The process is preferably performed in a solvent such as toluene, xylene, heptane or hexane, an ether solvent such as tetrahydrofuran or dimethoxyethane, or a chlorinated solvent such as monochlorobenzene, dichlorobenzene, chlorobutane or methylene chloride, or linear or branched alcohols of 1 to 6 carbon atoms, such as ethanol and more particularly n-butanol. The term "base" means the hydrogen carbonate, carbonate, phosphate or hydroxide of an alkali metal such as lithium, sodium, potassium or cesium, and more particularly anhydrous tripotassium phosphate. Alkali metal alkoxides such as sodium or potassium methoxide, ethoxide, t-amyloxide or t-butoxide may also be used. Finally, amine bases such as diisopropylethylamine, DBU, DBN or tetramethylguanidine may be used. The term "additive" means alkali metal or alkaline-earth metal iodides or bromides, and more particularly sodium iodide.

A subject of the invention is also a process characterized in that the compound of formula (V) is obtained by heating a compound of general formula (VI) in acidic medium.

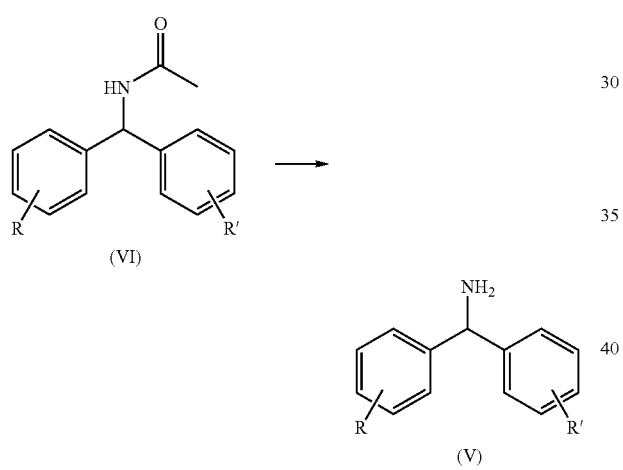

The process is preferably performed in a solvent such as linear or branched alcohols of 1 to 6 carbon atoms and more particularly n-butanol, or optionally as a mixture with water, in the presence of a strong mineral acid such as hydrobromic acid, sulfuric acid and more particularly hydrochloric acid, at a temperature of between 80° C. and 150° C.

A subject of the invention is also a process characterized in that the compound of formula (VI) is obtained from the compound of formula (VII) via a Ritter reaction in the presence of a nitrile and an acid catalyst.

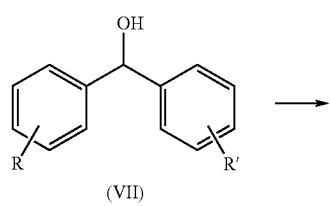

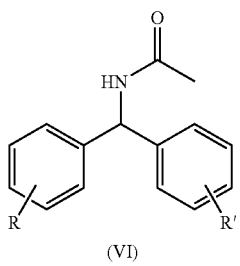

The process is preferably performed using a nitrile such as propionitrile, butyronitrile, benzonitrile, ethyl cyanoacetate or, more particularly, in the presence of acetonitrile. An acid catalysis is performed in the presence of sulfuric acid, methanesulfonic acid, trifluoromethanesulfonic acid, acetic acid, propionic acid or, more particularly, formic acid, at a temperature of between 50° C. and 150° C.

A subject of the present invention is thus also the three-step synthesis of the product of formla (IV)

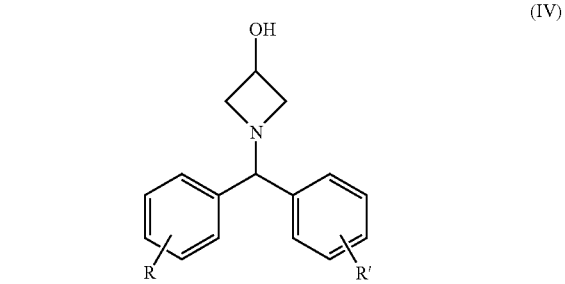

in which R and R' represent, independently of each other, one or more hydrogen, halogen (Cl, F, Br or I), cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy radicals, a) a product of formula (VII)

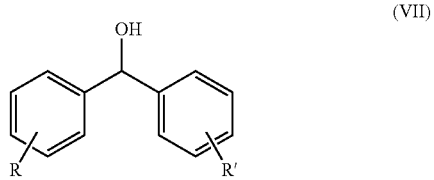

in which R and R' represent, independently of each other, one or more hydrogen, halogen (Cl, F, Br or I), cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy radicals, reacted with acetonitrile in the presence of catalysis with formic acid at a temperature of between 50° C. and 150° C., to give the product of formula (VI)

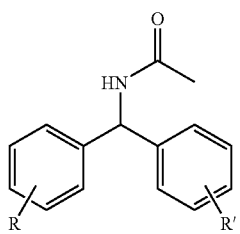

(VI)

in which R and R' represent, independently of each other, one or more hydrogen, halogen (Cl, F, Br or I), cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy radicals, b) the product of formula (VI) is converted by heating in acidic medium into a product of formula (V), or an acid salt thereof

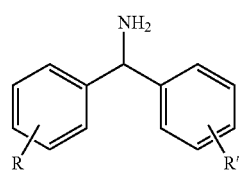

(V)

in which R and R' represent, independently of each other, one or more hydrogen, halogen (Cl, F, Br or I), cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy radicals, c) the product of formula (V) is converted into the product of formula (IV) in an organic solvent such as n-butanol, in the presence of the base anhydrous tripotassium phosphate, the additive sodium iodide and, where appropriate, an aqueous phase.

A subject of the invention is also a process according to the text hereinabove, characterized in that the compound of formula (VII) is obtained by reducing a benzophenone of formula (VIII), in the presence of a reducing agent at a temperature of from −40° C. to +30° C. Depending on the nature of the reducing agent, the reaction is performed in ethers such as tetrahydrofuran or dimethoxyethane, aromatic solvents such as toluene, chlorinated solvents such as dichloromethane, alcohols such as methanol or ethanol, or water. The reducing agents used may be sodium borohydride, lithium borohydride, lithium aluminum hydride or diisobutylaluminum hydride.

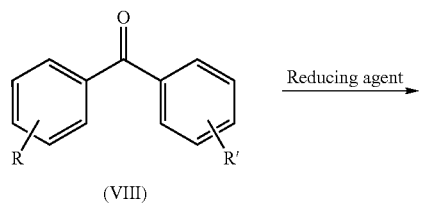

(VIII)

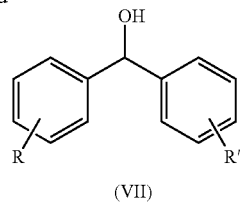

(VII)

The intermediate (V) may also be obtained directly from the intermediate (VIII) by using the Leuckart reaction via an intermediate (IX).

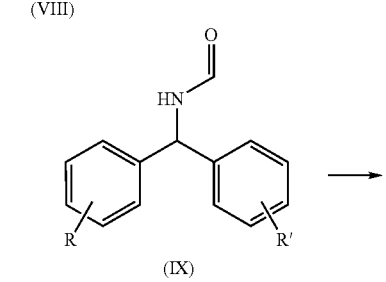

(VIII)

(IX)

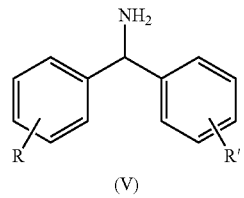

(V)

The reaction for formation of (IX) is performed in the presence of formic acid, ammonium formate and formamide at 170-175° C., or of formamide with catalysis using magnesium chloride. The deformylation of (IX) is performed in the presence of HCl in water or methanol. The deformylation of (IX) is performed under conditions similar to those used for the conversion of VI to V.

A subject of the present invention is thus also a process for synthesizing the product (V), characterized by a) formation of N-[bis(4-chlorophenyl)methyl]formamide (IX) from bis(4-chloro-phenyl)methanone in the presence of formamide with catalysis using magnesium chloride, b) deformylation in the presence of HCl in methanol, to give [bis(4-chloro-phenyl)methyl]amine.

Compared with patent application WO 01/64634, this novel process provides improvements in terms of safety, but also a simplification of the steps for the purification and isolation of the intermediates or of the finished product, especially by chromatography on silica, to replace them with crystallizations, thus making the process compatible with industrial production. By way of example, the reaction scheme below illustrates, in a non-limiting manner, the reagents used for each of the steps and for which R and R' represent chlorines in the para position and R" represents a fluorine in positions 3 and 5, R'" is a methyl, the solvent is toluene, the base is tripotassium phosphate and the phase-transfer agent is tris(dioxa-3,6-heptyl)amine (TDA-1), and N-{1-[bis(4-chlorophenyl)methyl]azetidin-3-yl}-N-(3,5-difluorophenyl)methylsulfonamide is obtained.

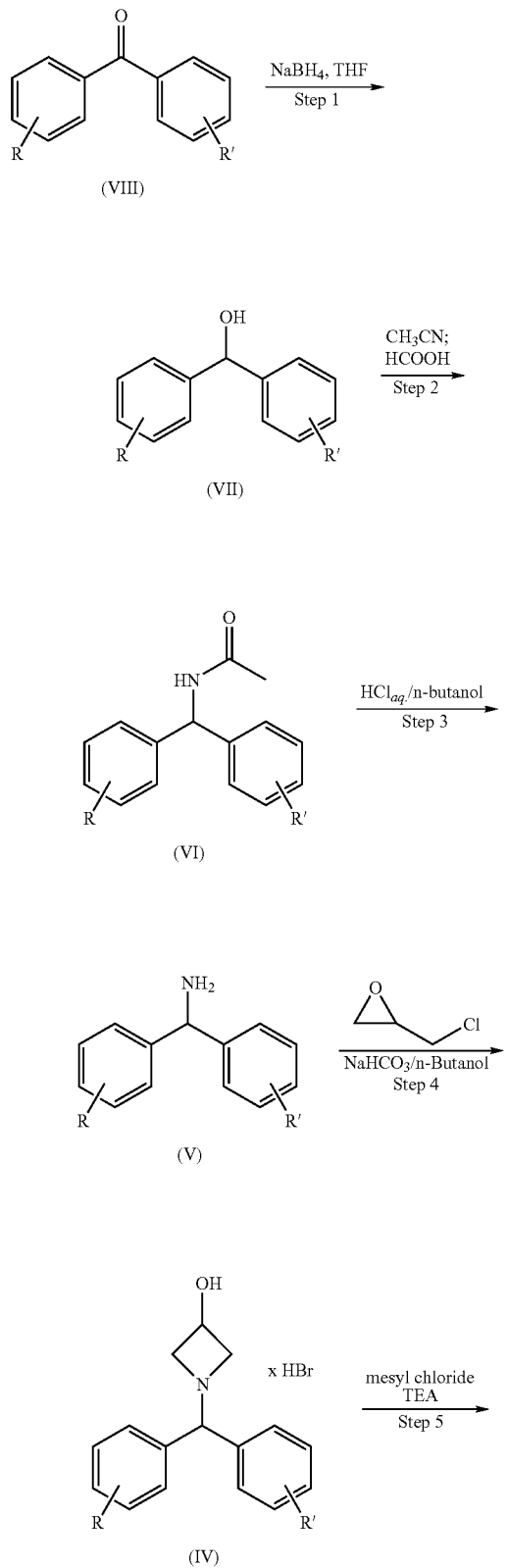

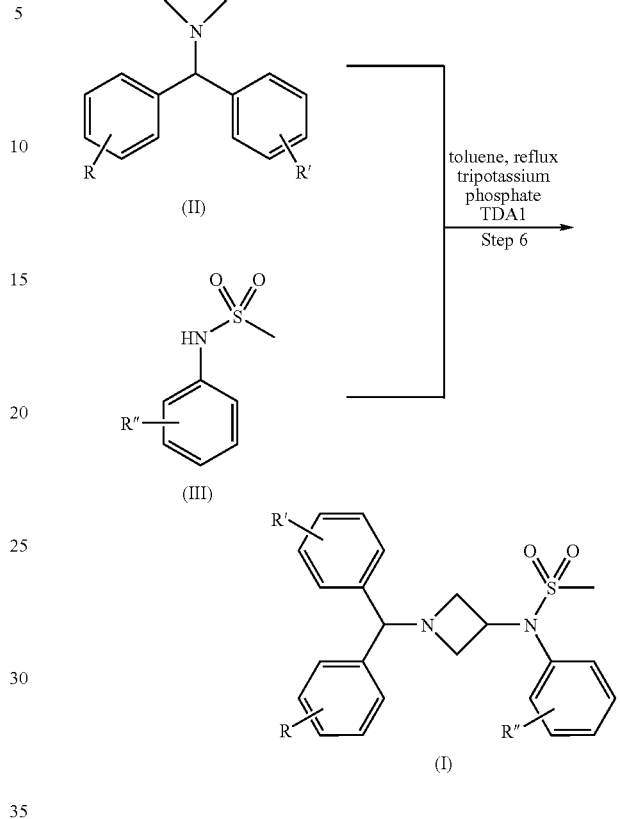

Experimental Section for the Synthesis of N-{1-[bis(4-chlorophenyl)methyl]azetidin-3-yl}-N-(3,5-difluorophenyl)methylsulfonamide Step 1

50 g of 4,4'-dichlorobenzophenone and 300 ml of THF are introduced, at a temperature of 20±2° C., into a four-necked one-liter flask equipped with a mechanical stirrer and a temperature probe, and placed under a nitrogen atmosphere. 54 ml (0.32 mol per mole of product) of sodium borohydride solution (solution prepared extemporaneously with 2.7 g of sodium borohydride, 0.135 ml of 32% sodium hydroxide and 54 ml of demineralized water) are added over 1 hour under nitrogen, at 20±2° C.

The solution obtained is stirred for 3 hours at 20±2° C. 230 ml of 1N hydrochloric acid are then added over 60 minutes at 20-22° C. The aqueous phase is separated out by settling and the organic phase containing the 4,4-dichlorobenzhydrol is used directly in step 2.

Step 2

The 4,4'-dichlorobenzydrol solution is introduced at 20±2° C. into a four-necked two-liter flask equipped with a mechanical stirrer and a temperature probe, and placed under an inert nitrogen atmosphere, and is then heated to between 68 and 75° C. and concentrated at atmospheric pressure to 80 ml. The solution is cooled to 50±5° C. and 300 ml of acetonitrile are added in a single portion.

250 ml of acetonitrile are distilled off at ordinary pressure, and a further 100 ml of acetonitrile are then added in a single portion. 150 ml of acetonitrile are distilled off with stirring, at atmospheric pressure.

The solution is then cooled to 65±5° C. and 200 ml of formic acid are added over 10 minutes while keeping the temperature at 65±5° C.

The two-phase solution is refluxed (103° C.) for 5 hours with vigorous stirring, under a stream of nitrogen. The solution is cooled with stirring to 80±2° C. and 750 ml of demineralized water are added over 30 minutes. The suspension obtained is stirred for 30 minutes at 80±2° C. and then cooled to between +5° C. and +10° C. over 30 minutes and maintained at this temperature for 1 hour.

The solid is filtered off by suction and washed by slurrying with 3×100 ml of demineralized water.

The N[bis(4-chlorophenyl)methyl]acetamide is obtained in a yield of 95%.

Step 3

50 g of N-[bis(4-chlorophenyl)methyl]acetamide, 250 ml of n-butanol and 150 ml of demineralized water, are introduced at 20±2° C., into a four-necked one-liter flask equipped with a mechanical stirrer and a temperature probe, and placed under a nitrogen atmosphere.

135 ml of 37% hydrochloric acid are then added over 15 minutes; the mixture is exothermic and the temperature rises to 32° C., the dissolution is partial and the mixture is two-phase. The reaction mixture is refluxed (93° C.) for 15 hours with stirring, under nitrogen. 125 ml of demineralized water are added in a trickle over about 5 minutes with stirring at reflux, under nitrogen. 350 ml of reaction medium are distilled off at atmospheric pressure. The temperature rises to 103° C.

The crystallization is completed by adding 125 ml of demineralized water in a trickle, while maintaining the reflux (105° C.).

The suspension is cooled to 10±2° C. over 30 minutes and is then maintained at this temperature for 1 hour. The medium is cooled and washed by displacement with 50 ml of demineralized water.

The [bis(4-chlorophenyl)methyl]amine hydrochloride is obtained in a yield of 98%.

Step 4

50 g of [bis(4-chlorophenyl)methyl]amine hydrochloride, 300 ml of n-butanol and 17.5 g of sodium bicarbonate are introduced, at 20±2° C., into a four-necked one-liter flask equipped with a mechanical stirrer and a temperature probe, and placed under a nitrogen atmosphere. A white suspension is obtained, which is heated to 80±2° C.

This temperature is maintained for 1 hour. The medium is cooled to 20±2° C. and 29.6 g of epichlorohydrin are added in a trickle (about 5 minutes) at 20±2° C. The medium is heated with stirring, under nitrogen, at 80±2° C. for 4 hours.

The reaction medium is then cooled to 40±2° C., after which 31.4 g of tripotassium phosphate and 0.29 g of sodium iodide are added.

The reaction medium is refluxed (108-109° C.) for 3 hours. It is then cooled over about 1 hour to 20±2° C. and maintained at this temperature overnight. 250 ml of demineralized water are added at 20±2° C. and the whole mixture is stirred at this temperature for 30 minutes. The aqueous phase is separated out by settling and the organic phase is washed with 2×250 ml of demineralized water.

The organic solution is concentrated at atmospheric pressure to 100 ml.

A yellow solution is obtained, to which is added 500 ml of toluene, and the reaction medium is then distilled to constant volume, at ordinary pressure, while maintaining the level by adding toluene (350 ml). The temperature at the end of entrainment is 110° C.

The reaction medium is then cooled to 20±2° C. and about 10 ml of a 62% solution of hydrobromic acid in water are added over 5 minutes.

The crystallization is seeded with 0.01 g of 1-[bis(4-chlorophenyl)methyl]azetidin-3-ol hydrobromide.

The medium is stirred under nitrogen at 20±2° C. for 30 minutes. About 10 ml of a 62% solution of hydrobromic acid in water are then added over 5 minutes with stirring, under nitrogen, at 20±2° C. The mixture is maintained at this temperature for 30 minutes. The medium is then filtered by suction and washed by displacement with 2×50 ml of toluene.

The 1-[bis(4-chlorophenyl)methyl]azetidin-3-ol hydrobromide is thus obtained in a yield of 75.8%.

Step 5

50 g of 1-[bis(4-chlorophenyl)methyl]azetidin-3-ol hydrobromide and 250 ml of methylene chloride are introduced, at 20±2° C., into a four-necked one-liter flask equipped with a mechanical stirrer and a temperature probe, and placed under a nitrogen atmosphere, followed by addition of 53.6 ml of triethylamine over 5 minutes. The temperature rises to 27° C. The mixture is stirred for 30 minutes while allowing the temperature to change, which falls to +22° C. The medium is cooled to −10±2° C. and 14.9 ml of methanesulfonyl chloride are added at −10±2° C. over about 15 to 30 minutes. The white suspension is maintained at −10±2° C. for 2 hours. 200 ml of a solution containing 50 g/l of sodium hydrogen carbonate are added over 10 minutes, while allowing the temperature to rise to between +10 and +15° C. The dissolution is complete and the medium is maintained at between +10 and +15° C. for 30 minutes. The medium is separated into phases by settling and the organic solution is washed with 2×50 ml of a solution containing 50 g/l of sodium hydrogen carbonate, at between +10 and +15° C. The solution of 1-[bis(4-chlorophenyl)methyl]azetidin-3-yl methanesulfonate in methylene chloride is concentrated with stirring, under a vacuum of 50 mbar, to 100 ml.

Step 6

425 ml of toluene are added to the solution of 1-[bis(4-chlorophenyl)methyl]azetidin-3-yl methanesulfonate in methylene chloride.

The solution is distilled with stirring, under a vacuum of 50 mbar, at an internal temperature of less than 60° C., while keeping the level constant by adding 200 ml of toluene. The solution is cooled with stirring, under nitrogen, to 20° C. and 32.7 g of anhydrous tripotassium phosphate, 8 ml of tris(dioxa-3,6-heptyl)amine and 27 g of N-(3,5-difluorophenyl) methylsulfonamide are added. This suspension is refluxed (112° C.) for 20 hours. The medium is cooled to 25° C. 250 ml of demineralized water are added in a single portion. The medium is separated into phases by settling and the organic phase is washed with 2×250 ml of demineralized water.

The organic phase is concentrated to 100 ml, under a vacuum of 50 mbar, at a temperature below 50° C. 750 ml of isopropyl alcohol are added and the distillation is continued under vacuum, while keeping the level constant by adding 500 ml of isopropyl alcohol. The recrystallization starts during the distillation. The medium is refluxed to dissolve the majority of the product, and is then cooled with stirring, under nitrogen, to 20° C. over about 30 minutes (recrystallization at about 70° C.) and is maintained for 1 hour under these conditions. After filtering off by suction and washing with isopropyl alcohol (2×50 ml), N-{1-[bis(4-chlorophenyl)methyl]-azetidin-3-yl}-N-(3,5-difluorophenyl) methylsulfonamide is obtained in a yield of 79.2%.

Access to Compound IX 10 g of bis(4-chlorophenyl)methanone, 30 g of formamide and 0.81 g of magnesium chloride hexahydrate are introduced into a four-necked 100 ml flask equipped with a magnetic stirrer, a temperature probe, a nitrogen inlet and a sparge outlet. The suspension is heated at 170±5° C. for about 3 hours.

The medium is cooled to about 100° C. and 30 ml of water are then introduced over about 15 minutes with vigorous stirring. The mass crystallizes during the addition of water and, after cooling to about 20±5° C., the medium is filtered by suction and washed by displacement with 3×10 mL of water.

The N-[bis(4-chlorophenyl)methyl]formamide is obtained in a yield of 93%.

Access to Compound V 50 g of N-[bis(4-chlorophenyl)methyl]formamide and 250 ml of methanol are introduced into a four-necked one-liter flask equipped with a crescent-shaped mechanical stirrer, a temperature probe, a nitrogen inlet and a sparge outlet, followed by addition of 23 ml of 37% hydrochloric acid. The medium is heated at the reflux temperature of the methanol for about 2 hours. After cooling to 65±5° C., the medium is neutralized by adding a solution of 38.2 g of sodium carbonate in 250 ml of water, over about 30 minutes. After cooling to 10±2° C., the medium is filtered by suction and washed by displacement with 2×20 ml of water.

The [bis(4-chlorophenyl)methyl]amine is obtained in this form in a yield of 98%.

What is claimed is:

1. A process for the preparation of [bis(4-chlorophenyl)methyl]amine, comprising:
    a) reacting bis(4-chloro-phenyl)methanone and formamide in the presence of a catalyst, magnesium chloride to form N-[bis-(4-chlorophenyl)methyl]formamide; and
    b) deformylating N-[bis-(4-chlorophenyl)methyl]formamide in the presence of HCl in methanol to give [bis(4-chlorophenyl)methyl]amine.

2. A process for the preparation of a compound of formula (IV):

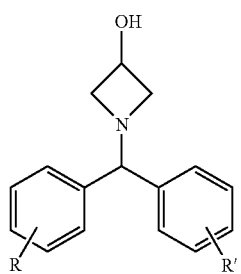

(IV)

wherein
R and R' represent, independently of each other, one or more hydrogen, halogen, halogen, cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy;

comprising the steps of:
a) reacting a compound of formula (VII)

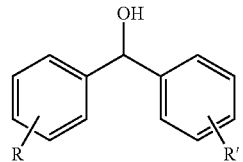

(VII)

wherein
R and R' represent, independently of each other, one or more hydrogen, halogen halogen, cyano, nitro, linear or branched alkyl of 1 to 6 carbon atoms, linear or branched alkoxy of 1 to 6 carbon atoms, linear or branched alkyl carboxylate of 1 to 6 carbon atoms, trifluoromethyl or trifluoromethoxy;

with acetonitrile in the presence of formic acid at a temperature in the range of from about 50° C. to about 150° C., to form a compound of formula (VI):

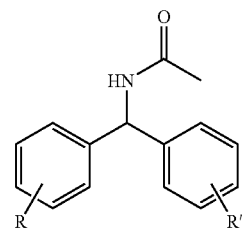

(VI)

wherein R and R' are as defined above;

b) heating the compound of formula (VI) in an acidic medium to form a compound of formula (V) or an acid salt thereof:

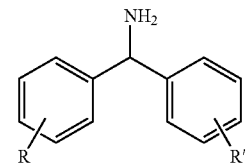

(V)

wherein R and R' are as defined above; and c) converting the compound of formula (V) into the compound of formula (IV) in an organic solvent, n-butanol, and in the presence of anhydrous tripotassium phosphate, an additive, sodium iodide, and, where appropriate, optionally in an aqueous phase.

* * * * *